US008897884B2

(12) United States Patent
Snitting (10) Patent No.: US 8,897,884 B2
(45) Date of Patent: Nov. 25, 2014

(54) IMPLANTABLE MEDICAL DEVICE WITH A VOLTAGE PROTECTION CIRCUIT (75) Inventor: Tomas Snitting, Stockholm (SE)

(73) Assignee: St. Jude Medical AB, Jarfalla (SE)

( * ) Notice: Subject to any disclaimer, the term of this patent is extended or adjusted under 35 U.S.C. 154(b) by 2152 days.

(21) Appl. No.: 11/667,714

(22) PCT Filed: Nov. 26, 2004

(86) PCT No.: PCT/SE2004/001755
§ 371 (c)(1),
(2), (4) Date: Feb. 3, 2009

(87) PCT Pub. No.: WO2006/057587
PCT Pub. Date: Jun. 1, 2006

(65) Prior Publication Data
US 2009/0132007 A1 May 21, 2009

(51) Int. Cl.
A61N 1/00 (2006.01)
A61N 1/02 (2006.01)
A61N 1/372 (2006.01)
A61N 1/08 (2006.01)
A61N 1/37 (2006.01)

(52) U.S. Cl.
CPC .......... *A61N 1/37229* (2013.01); *A61N 1/025* (2013.01); *A61N 1/3718* (2013.01); *A61N 1/08* (2013.01); *A61N 1/372* (2013.01)
USPC .......................................................... 607/60

(58) Field of Classification Search
USPC ................................................ 607/32, 60, 63
See application file for complete search history.

(56) References Cited

U.S. PATENT DOCUMENTS

| 4,739,437 | A | 4/1988 | Morgan |
| 5,584,870 | A | 12/1996 | Single et al. |
| 6,505,072 | B1 * | 1/2003 | Linder et al. .............. 607/32 |
| 8,239,026 | B2 * | 8/2012 | Dahlberg .................. 607/37 |
| 2003/0236077 | A1 | 12/2003 | Sivard |
| 2004/0122490 | A1 | 6/2004 | Reinke et al. |

FOREIGN PATENT DOCUMENTS

| EP | 0 598 617 | 5/1994 |
| WO | WO 97/12645 | 4/1997 |

* cited by examiner

Primary Examiner — Eric D. Bertram (57) ABSTRACT

An implantable medical device has an electronic circuit and a telemetry circuit both connected to a common ground, and at least one RF telemetry antenna that is formed by a number of parts of the implantable device that are capable of functioning as an antenna. When implanted, these parts are in contact with tissue. For voltage protection, the RF antenna circuit is connected to the parts of the RF telemetry antenna via at least one capacitor. The capacitor is dimensioned to withstand a voltage amplitude of a pulse that would be capable of modifying the state of, or destroying, any component in the RF telemetry circuit or the electronic circuit.

10 Claims, 7 Drawing Sheets

IMPLANTABLE MEDICAL DEVICE WITH A VOLTAGE PROTECTION CIRCUIT

BACKGROUND OF THE INVENTION

1. Field of the Invention

The present invention generally relates to implantable medical devices such as implantable cardiac pacemakers and implantable cardioverter/defibrillators, and in particular to protection circuits for protecting the electronic circuits and telemetry circuits of such a device.

2. Description of the Prior Art

Implantable medical devices, including cardiac rhythm management devices such as pacemakers and implantable cardioverter/defibrillators, typically have the capability to communicate data with an external programmer via a radio-frequency telemetry link. A clinician may use such an external programmer to program the operating parameters of an implanted medical device. For example, the pacing and other operating characteristics of a pacemaker are typically modified after implantation in this manner. Modern implantable devices also include the capability for bidirectional communication so that information can be transmitted to the programmer from the implanted device. Among the data which may typically be telemetered from an implantable device are various operating parameters and physiological data. The implantable device generates and receives the radio signals by means of an antenna. Today, antennas capable of far-field communications are of increasing interest in implantable medical devices, in order to allow communication over much greater distances than with inductively coupled antennas.

The technology of cardiac pacemakers has developed in sophistication and functionality over the years. In general, cardiac pacemakers are designed to control the heart by correcting or compensating for various heart abnormalities which can be encountered in human patients. For example, cardiac pacemakers may provide therapeutic stimulation to the heart by delivering therapeutic pulses such as pacing, cardioversion or defibrillation pulses. With this increasing sophistication, however, a concomitant increase has occurred in sensitivity of the implantable devices to misoperation due to external influences such as defibrillation, electrocautery, and the like. Such interference or voltage pulses may be received by the antenna, for example, at galvanic exposure against tissue and may be conducted further into the electronic circuits and RF telemetry circuits of the medical device or may be conducted into the circuits, which is undesirable. This may cause the medical device to falsely identify the interference as being of cardiac origin and give rise to, for example, an erroneous output rate, or in the worst case, it may change the state of or destroy components of the circuits, which, in turn, may severely damage the functions of the medical device.

Hence, there is a need of a circuit that in an effective way can protect the internal circuits of an implanted medical device against undesired voltage pulses caused by exposure to e.g. defibrillation and/or electrocautery.

SUMMARY OF THE INVENTION

An object of the present invention is to provide protection circuits that can effectively protect the internal circuits of an implanted medical device against undesired voltage pulses caused by exposure to defibrillation and/or electrocautery received by the antenna, for example, at galvanic exposure against tissue and be conducted further into the electronic circuits and RF telemetry circuits of the medical device.

According to the present invention, this object is achieved by an implantable medical device having at least one electronic circuit connected to common ground; at least one RF telemetry circuit connected to the common ground; at least one RF telemetry antenna, the antenna being in tissue contact; and wherein each part of the implantable device capable of functioning as an antenna being in tissue contact and connected to the RF telemetry circuit is connected via at least one capacitor, the at least one capacitor being arranged to withstand the voltage amplitude of a pulse capable of modifying state of or destroying at least one component of said RF telemetry circuit or the electronic circuit.

The invention is based arranging a capacitance as a filter circuit for blocking voltage transients or pulses, due to exposure to defibrillation and/or electrocautery conducted into the device due to galvanic contact between the RF circuits of the device and tissue via a part of the device functioning as an antenna, for example, via a housing of the device or via an antenna external to the housing in tissue contact and capable of modifying state of or destroying at least one component of the RF telemetry circuit or the electronic circuit from reaching the components. The capacitor is dimensioned to withstand the voltage pulse.

This solution provides several advantages. One advantage is that the capacitors are small which is of high importance in implanted medical devices. Another advantage is that the capacitor has a simple design which therefore easily can be incorporated into the circuits of the medical device.

In an embodiment of the present invention, the medical device has a least one capacitor connected in series with the antenna, and the capacitor is arranged to withstand the voltage amplitude of a voltage transient received by the antenna or the housing that would be capable of modifying the state of or destroying at least one component of the RF telemetry circuit or the electronic circuit.

In another embodiment, at least one capacitor is connected to a housing of the medical device and to the common ground, and the capacitor is arranged to withstand the voltage amplitude of a voltage transient received by the housing that would be capable of modifying the state of or destroying at least one component of the RF telemetry circuit or the electronic circuit.

In preferred embodiments, the medical device has at least one antenna matching network, and the first capacitor is arranged in the antenna matching network. By dimensioning the capacitor to constitute a part of the antenna matching network the signal losses in the circuits can be reduced.

In a preferred embodiment of the present invention, the first capacitor is arranged in a feedthrough for the antenna in the housing of the medical device. This makes the circuit is even more efficient with respect to the required space.

In another embodiment of the present invention, the antenna of the implantable medical device is arranged for communication in at least two specified frequency bands and the antenna matching network is arranged to match the antenna impedance to the RF telemetry circuit at the specific frequency bands.

According to a specific embodiment of the present invention, the implantable medical device has a first antenna matching network tuned for a first specific frequency band; and a second antenna matching network tuned for a second specific frequency band. The capacitor is connected in series with the first antenna matching network and to the second antenna matching network and is arranged to interact with each of the first and the second antenna matching networks to match the antenna impedance to the RF telemetry circuit at the specific frequency bands. Accordingly, the capacitor is dimensioned to function as a component in a duplex filter so that signals having a frequency in the first frequency band sees a low impedance in the branch including first antenna matching network and a high impedance at the other branch, while the opposite conditions applies at the second frequency. Thus, any additional RF filter to separate the two frequencies for the first RF telemetry circuit and the second RF telemetry circuit is not necessary. This is advantageous since the impedance matching is significantly simplified. Preferably, a first frequency band is provided for telemetry communication and a second frequency band is provided for wake-up signals. This entails that a power management scheme in which the RF telemetry circuitry are duty cycled based upon wakeups can be employed. Normally, the RF telemetry circuitry are in a low power state until powered up by a wake up signal to transmit or receive a message. Consequently, the life span of the battery of the medical device can be lengthened. United States Patent Application Publication 2003/0236077 A1 discloses the concept of utilizing a second frequency band for wake-up signals.

DESCRIPTION OF THE PREFERRED EMBODIMENTS

Figure 1A:
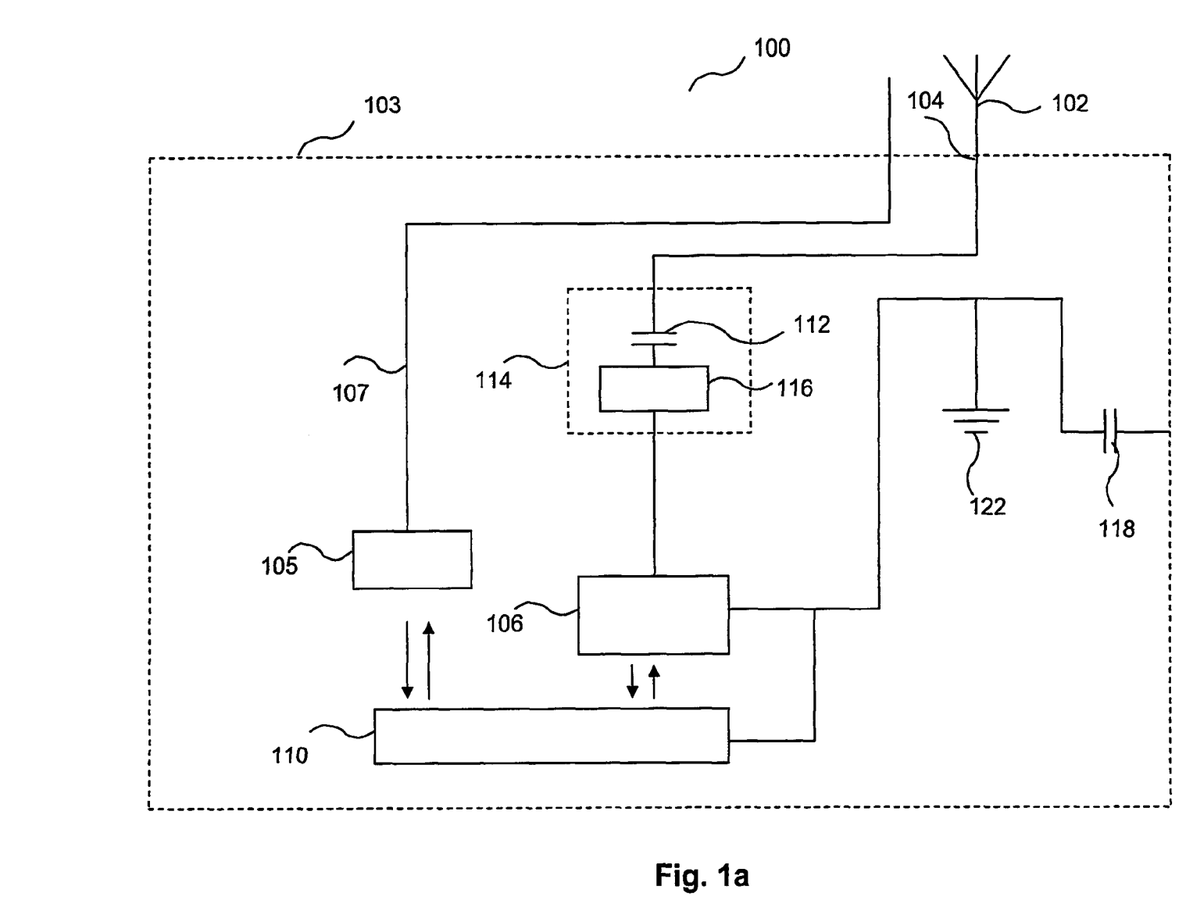
FIG. 1a diagrammatically shows an implantable medical device comprising protection circuits for protecting the electronic circuitry of the device against undesired voltage pulses caused by exposure to defibrillation and/or electrocautery conducted into the device due to galvanic contact between the RF circuits of the device and tissue via a part of the medical device capable of functioning as an antenna being in tissue contact and connected to electronic circuitry of the device in accordance with a first embodiment of the present invention.

FIG. 1a diagrammatically shows an implantable medical device (IMD) comprising protection circuits for protecting the electronic circuitry of the device against undesired voltage transients caused by exposure to defibrillation and/or electrocautery conducted into the device via a part of the medical device capable of functioning as an antenna being in tissue contact and connected to electronic circuitry of the device in accordance with a first embodiment of the present invention.

The IMD 100 is provided with an antenna 102 for communication with external devices such as an external programmer. Preferably, the antenna 102 is suitable for radiating and receiving far-field electromagnetic radiation. The antenna 102 is in direct tissue contact. It should be noted that the housing effectively is a part of the antenna and affects the radiation properties of the antenna 102. The housing is further in contact with the tissue. The IMD 100 includes a hermetically sealed housing 103 provided with an antenna feedthrough 104 through which the antenna 102 is located and feedthroughs for medical leads, which housing 103 typically is formed of a biocompatible metal, e.g. titanium. The housing 103 contains a therapy circuitry 105 for providing particular functionality to the device such as cardiac rhythm management, or neuromuscular stimulation, RF telemetry circuitry 106 for providing RF communications. A battery (not shown) supplies power to the electronic circuitry within the housing 103. One or more leads 107 are connected to the therapy circuitry 105, which lead or leads 107 may be unipolar or bipolar, and may be adapted to operate in cooperation with a wide variety of implantable medical devices. Moreover, the lead or the leads 107 may include any of the passive or active fixation mechanisms known in the art for fixation of the lead 107 to the cardiac tissue when final position has been found. As an example, lead distal tip (not shown) may include a tined tip or a fixation helix. The leads 107 also comprises one or more electrodes, such as a tip electrode or a ring electrode. The electrode senses electrical signals associated with depolarization and repolarization of the heart. In addition, the electrode may also transmit pacing pulses for causing depolarization of cardiac tissue adjacent to the electrode. Furthermore, the leads 107 also include sensing means arranged to sense signals related heart activity.

A microprocessor controller 110 controls the operation of the therapy circuit 105, which includes sensing and stimulus generation circuitry that are connected to the electrodes of the lead or leads 107 for control of heart rhythm, and the RF telemetry circuitry for transmitting and receiving a carrier signal at a specific frequency modulated with telemetry data.

The controller 110 also outputs and receives the data contained in the modulated carrier generated or received by the RF telemetry circuitry 106. The RF telemetry circuitry 106 includes an RF transmitter and receiver that are connected to the antenna 103.

A capacitor 112 is connected in series with the antenna 102 and is arranged to withstand a voltage amplitude of a pulse received by the antenna 102 and capable of modifying the state of or destroying components of the RF telemetry circuitry 106, the controller 110, or the therapy circuit 105. Preferably, the capacitor 112 is dimensioned to withstand a voltage exceeding 100 V, and, more preferably, to withstand a voltage in the range of 75-1000 V Furthermore, an antenna matching network 114 including matching circuits 116 arranged to adjust the impedance of the antenna 102 to the impedance of the RF telemetry circuitry 106 is connected to the antenna 102 and to the RF telemetry circuit 106. The antenna matching network 114 loads the antenna 102 with an amount of inductance or capacitance so as to adjust the effective electrical length of the antenna, and hence the resonance frequency of the antenna. By matching the antenna impedance to the impedance of the RF telemetry circuitry at a specific carrier frequency, the reactance of the antenna may be tuned out at that frequency so that the antenna forms a resonant structure and efficiently transmits/receives far-field radiation.

Moreover, the RF telemetry circuit 106 and the controller 110 are connected to common ground 122, which, in turn, is connected to the housing 103. In this embodiment, a second capacitor 118 is interposed between common ground 122 and the housing 103. The second capacitor is arranged to withstand a voltage amplitude of a pulse conducted into the circuits via the housing 103 and common ground 122 and capable of modifying the state of or destroying components of the RF telemetry circuitry 106, the controller 110, or the therapy circuit 105. Preferably, the second capacitor 118 is dimensioned to withstand a voltage exceeding 100 V, and, more preferably, to withstand a voltage in the range of 75-1000 V.

According to a preferred embodiment, the capacitor 112 is incorporated into the matching network 114 connected in series with the matching circuits 116 and is dimensioned to constitute a part of the antenna matching. It should be noted that the capacitor 112 is applicable also in IMD's not being provided with any antenna matching network.

Figure 1B:
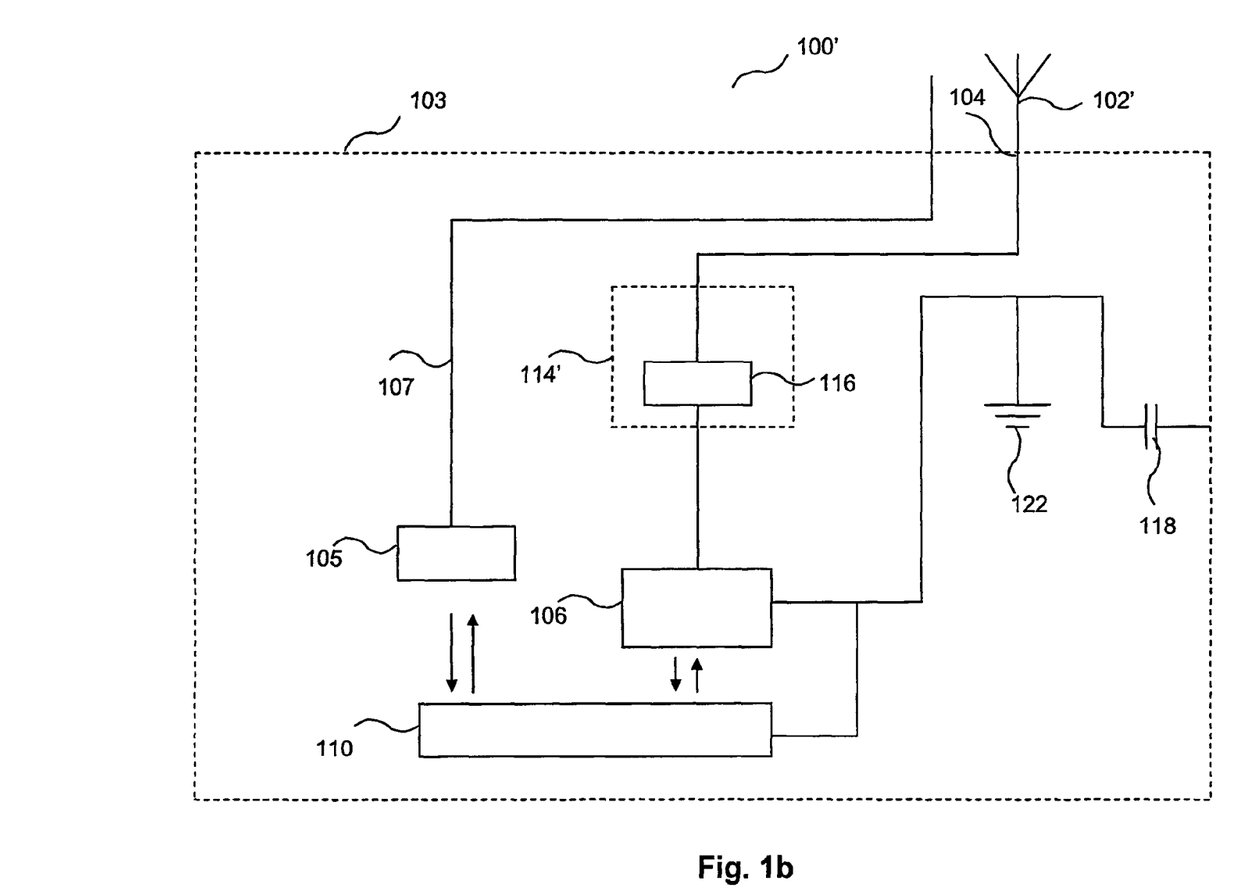
FIG. 1b diagrammatically shows an implantable medical device having an encapsulated monopole antenna and comprising protection circuits for protecting the electronic circuitry of the device against undesired voltage pulses caused by exposure to defibrillation and/or electrocautery conducted into the device due to galvanic contact between the RF circuits of the device and tissue via the housing in accordance with a second embodiment of the present invention.

With reference now to FIG. 1b, a second embodiment of the present invention will be described. FIG. 1b diagrammatically shows an implantable medical device having an encapsulated monopole antenna and comprising protection circuits for protecting the electronic circuitry of the device against undesired voltage pulses caused by exposure to defibrillation and/or electrocautery conducted into the device due to galvanic contact between the RF circuits of the device and tissue via the housing in accordance with a second embodiment of the present invention. Parts and elements shown in FIG. 1a that are similar or the same in this embodiment will be denoted with the same reference numerals and description thereof will be omitted. The IMD 100' is provided with an antenna 102' for communication with external devices such as an external programmer. The antenna 102' is a monopole antenna and is encapsulated and therefore not in direct tissue contact. In this second embodiment, a capacitor 118 is interposed between common ground 122 and the housing 103. The capacitor is arranged to withstand a voltage amplitude of a pulse conducted into the circuits via the housing 103 and capable of modifying the state of or destroying components of the RF telemetry circuitry 106, the controller 110, or the therapy circuit 105. Preferably, the second capacitor 118 is dimensioned to withstand a voltage exceeding 100 V, and, more preferably, to withstand a voltage in the range of 75-1000 V.

Preferably, the capacitor 118 is dimensioned such that it attains its self resonating frequency at the frequency band employed by the RF telemetry circuit 106, for example, the 400 MHz band. The effect at 400 MHz will be that the impedance is low or equal to the equivalent series resistance.

In the following, a number of alternative embodiments of the present invention will be described with reference to FIGS. 2-5.

Figure 2:
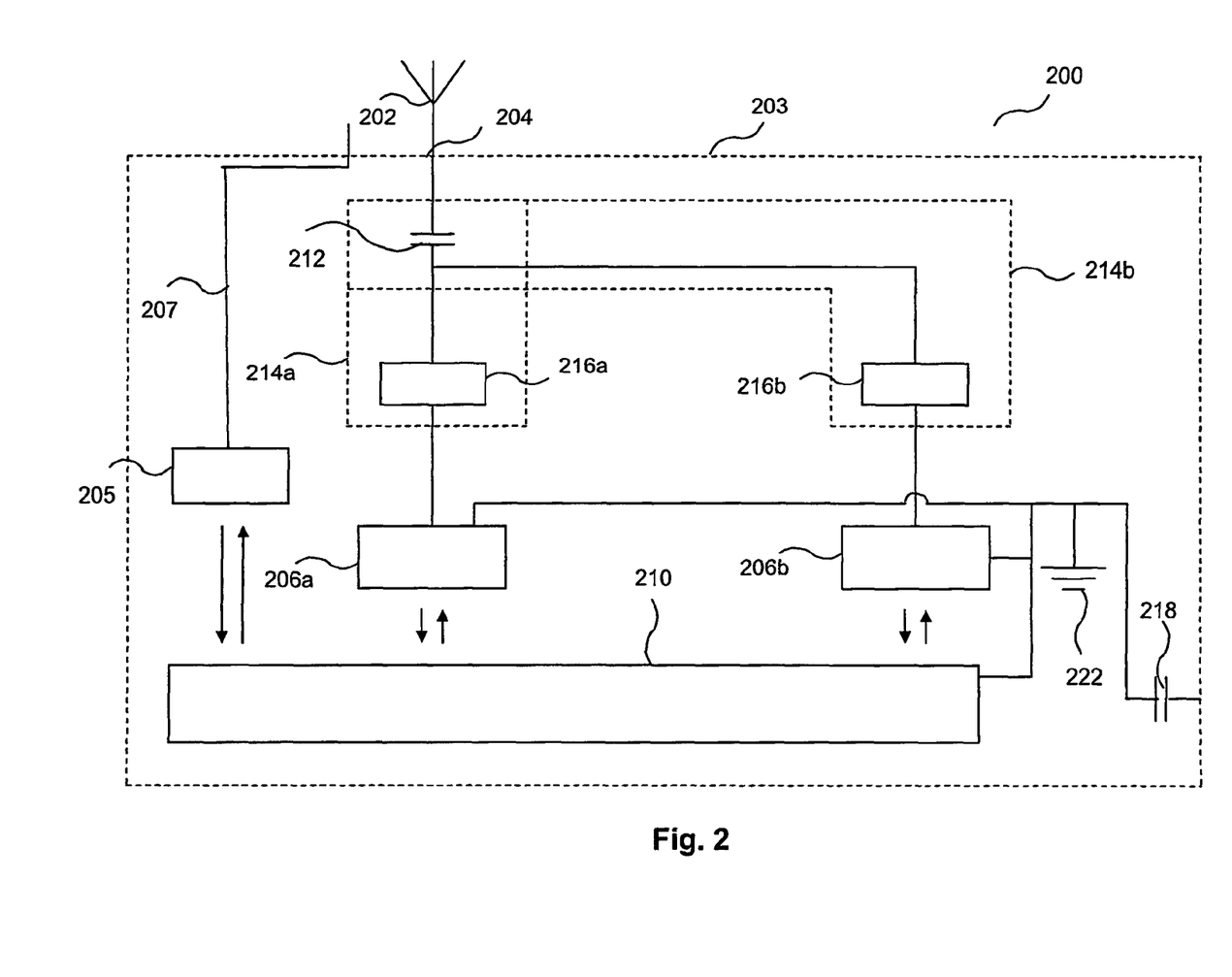
FIG. 2 diagrammatically shows a third embodiment of the implantable medical device comprising protection circuits in accordance with the present invention.

FIG. 2 diagrammatically shows an implantable medical device (IMD) comprising protection circuits for protecting the electronic circuitry of the device against undesired voltage pulses caused by exposure to defibrillation and/or electrocautery conducted into the device via a housing or via an antenna external to the housing in accordance with a third embodiment of the present invention. The IMD 200 is provided with an antenna 202 for communication with external devices such as an external programmer. Preferably, the antenna 202 is suitable for radiating and receiving far-field electromagnetic radiation. The antenna 202 is arranged for communication in two frequency bands. According to one example, the antenna 202 is arranged for RF-telemetry communication in a first frequency band at 400 MHz and a second frequency band at 2.45 GHz, wherein the first band is used for communication of data such as various operating parameters and physiological data and the second band is used for wake-up signals. The antenna 202 is located through an antenna feedhtrough 204 provided in housing 203 of the IMD 200. It should be noted that the housing effectively is a part of the antenna and affects the radiation properties of the antenna 202. The housing is further in contact with the tissue.

Furthermore, a therapy circuitry 205 for providing particular functionality to the device such as cardiac rhythm management, or neuromuscular stimulation, a first RF telemetry circuitry 206a for providing RF communications in the first frequency band, and a second RF telemetry circuitry 206b for providing RF communications in the first frequency band are arranged in the hermetically sealed housing 203. The first RF telemetry circuitry 206a comprises an RF transmitter and receiver connected to the antenna 202 and the second telemetry circuit 206b comprises an RF transmitter and receiver connected to the antenna 202. A battery (not shown) supplies power to the electronic circuitry within the housing 203. In this embodiment, the IMD 200 employs a power management scheme in which the RF telemetry circuitry 206a, 206b are duty cycled based upon wakeups. Normally, in this embodiment, the RF telemetry circuitry 206a, 206b are in a low power state until powered up by a wake up signal to transmit or receive a message. Furthermore, one or more leads 207 are connected to the therapy circuitry 205, which leads have been described above and which therefore are not further discussed.

A microprocessor controller 210 controls the operation of the therapy circuit 205, which includes sensing and stimulus generation circuitry that are connected to the electrodes of the lead or leads 207 for control of heart rhythm, and the RF telemetry circuitry for transmitting and receiving a carrier signal at a specific frequency modulated with telemetry data. The controller 210 also outputs and receives the data contained in the modulated carrier generated or received by the first RF telemetry circuitry 206a.

A capacitor 212 is connected in series with the antenna 202 and is arranged to withstand a voltage amplitude of a pulse received by the antenna 202 and capable of modifying the state of or destroying components of the first RF telemetry circuitry 206a, the second telemetry circuitry 206b, the controller 210, or the therapy circuit 205. According to one embodiment, the capacitor 212 is dimensioned for a voltage exceeding 100 V, and, more preferably, to withstand a voltage in the range of 75-1000 V.

Furthermore, a first antenna matching network 214a including matching circuits 216a is connected to the antenna 202 and to the first RF telemetry circuit 206a and is arranged to adjust the impedance of the antenna 202 to the impedance of the first RF telemetry circuitry 206a at the first frequency band at 400 MHz. By matching the antenna impedance to the impedance of the first RF telemetry circuitry at the first frequency band, the reactance of the antenna 202 may be tuned out at that frequency so that the antenna 202 forms a resonant structure and efficiently transmits/receives far-field radiation.

In addition, a second antenna matching network 214b including matching circuits 216b is connected to the second RF telemetry circuit 206b and is arranged to adjust the impedance of the antenna 202 to the impedance of the second RF telemetry circuitry 206b at the second frequency band at 2.45 GHz. By matching the antenna impedance to the impedance of the second RF telemetry circuitry 206b at the second frequency band, the reactance of the antenna 202 may be tuned out at that frequency so that the antenna 202 forms a resonant structure and efficiently transmits/receives far-field radiation.

Preferably, the capacitor 212 is incorporated into the first and the second antenna matching network 214a and 214b, respectively, and is connected in series with the matching circuits 216a, 216b, respectively. The capacitor 212 is dimensioned to constitute a part of the antenna matching at the first frequency band and the second frequency band, respectively. Preferably, the capacitor 212 is dimensioned such that it, at the first frequency band at 400 MHz, attains its self resonating frequency, or at least a low inductance or reactance, whilst it for the second frequency band at 2.45 GHz discloses a low inductance or reactance. Accordingly, the effect will be that the impedance at 400 MHz is low or equal to the equivalent series resistance. Thus, the capacitor 212 will function as a component in a duplex filter.

Moreover, the RF telemetry circuits 206a, 206b and the controller 210 are connected to common ground 222, which, in turn, is connected to the housing 203. In this embodiment a second capacitor 218 is interposed between common ground 222 and the housing 203. The second capacitor is arranged to withstand a voltage amplitude of a pulse conducted into the circuits via the housing 203 and common ground 222 and capable of modifying the state of or destroying components of the RF telemetry circuitry 206a, 206b, the controller 210, or the therapy circuit 205. Preferably, the second capacitor 118 is dimensioned to withstand a voltage exceeding 100 V, and, more preferably, to withstand a voltage in the range of 75-1000 V.

Preferably, the second capacitor 218 is dimensioned such that it attains its self resonating frequency at the frequency band employed by the first RF telemetry circuit 206a, for example, the 400 MHz band. The effect at 400 MHz will be that the impedance is low or equal to the equivalent series resistance.

Figure 3:
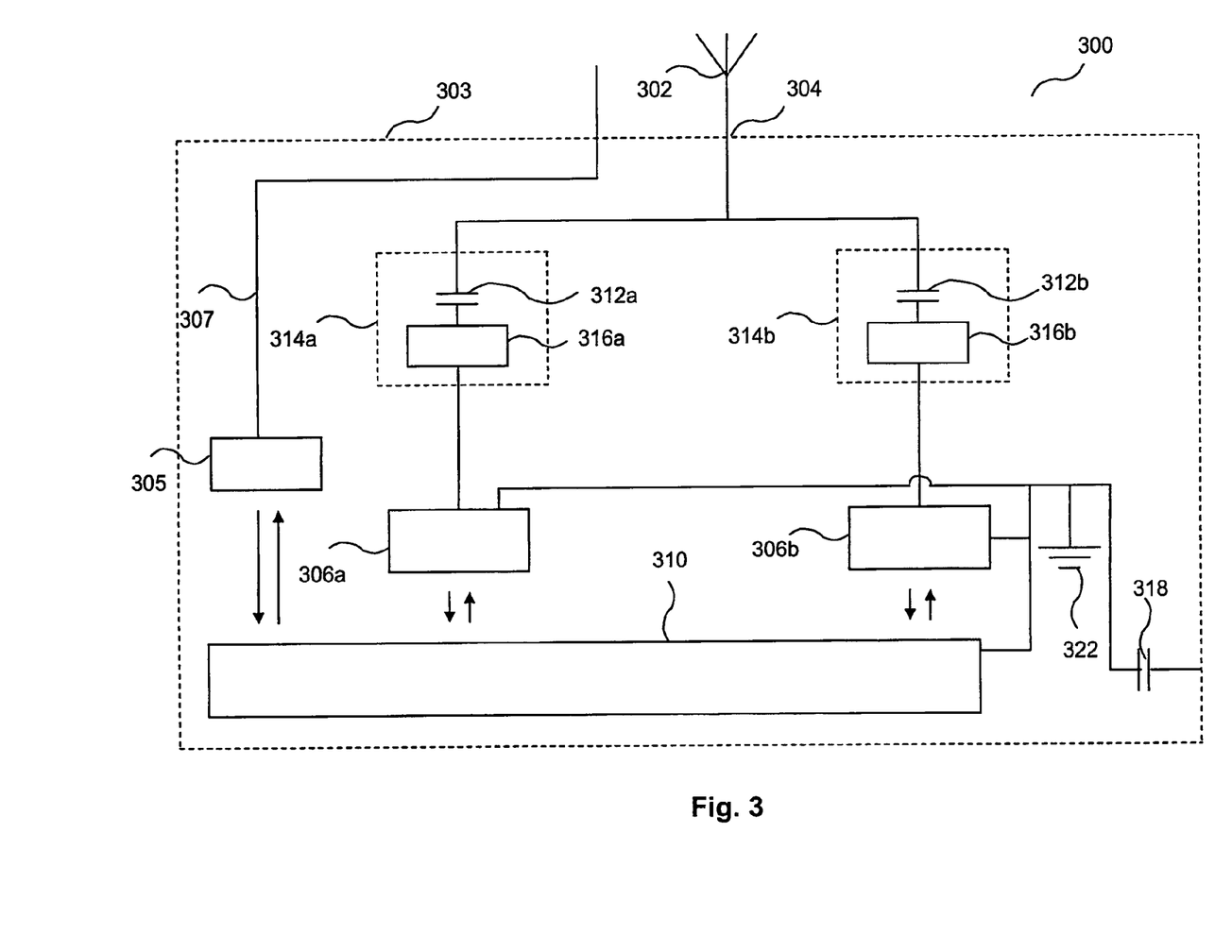
FIG. 3 diagrammatically shows fourth embodiment of the implantable medical device comprising protection circuits in accordance with the present invention.

FIG. 3 diagrammatically shows an implantable medical device (IMD) comprising protection circuits for protecting the electronic circuitry of the device against undesired voltage pulses caused by exposure to defibrillation and/or electrocautery conducted into the device via a housing or via an antenna external to the housing in accordance with a fourth embodiment of the present invention. The IMD 300 is provided with an antenna 302 suitable for radiating and receiving far-field electromagnetic radiation. The antenna 302 is arranged for communication in two frequency bands. According to one example, the antenna 302 is arranged for RF-telemetry communication in a first frequency band at 400 MHz and a second frequency band at 2.45 GHz, wherein the first band is used for communication of data such as various operating parameters and physiological data and the second band is used for wake-up signals. The antenna 302 is located through an antenna feedthrough 304 provided in housing 303 of the IMD 300. It should be noted that the housing effectively is a part of the antenna and affects the radiation properties of the antenna 302. The housing is further in contact with the tissue.

Furthermore, a therapy circuitry 305 for providing particular functionality to the device such as cardiac rhythm management, or neuromuscular stimulation, a first RF telemetry circuitry 306a for providing RF communications in the first frequency band, and a second RF telemetry circuitry 306b for providing RF communications in the first frequency band are arranged in the hermetically sealed housing 303. The first RF telemetry circuitry 306a comprises an RF transmitter and receiver that are connected to the antenna 302. Furthermore, the second telemetry circuit 306b also comprises an RF transmitter and receiver that are connected to the antenna 302. A battery (not shown) supplies power to the electronic circuitry within the housing 303. In this embodiment, the IMD 300 employs a power management scheme in which the RF telemetry circuitry 306a, 306b are duty cycled based upon wake-ups. Normally, in this embodiment, the RF telemetry circuitry 306a, 306b are in a low power state until powered up by a wake up signal to transmit or receive a message. Furthermore, one or more leads 307 are connected to therapy circuitry 305, which leads have been described above and which therefore are not further discussed.

A microprocessor controller 310 controls the operation of the therapy circuit 305, which includes sensing and stimulus generation circuitry that are connected to the electrodes of the lead or leads 307 for control of heart rhythm, and the RF telemetry circuitry for transmitting and receiving a carrier signal at a specific frequency modulated with telemetry data. The controller 310 also outputs and receives the data contained in the modulated carrier generated or received by the first RF telemetry circuitry 306a.

A first capacitor 312a is connected in series with the antenna 302 and is arranged to withstand a voltage amplitude of a pulse received by the antenna 302 and capable of modifying the state of or destroying components of the first RF telemetry circuitry 306a, the controller 310, or the therapy circuit 305. According to this embodiment, the first capacitor 312a is dimensioned for a voltage exceeding 100 V, and, more preferably, to withstand a voltage in the range of 75-1000 V. Additionally, a second capacitor 312b is connected in series with the antenna 302 and is arranged to withstand a voltage amplitude of a pulse received by the antenna 302 and capable of modifying the state of or destroying components of the second RF telemetry circuitry 306b, the controller 310, or the therapy circuit 305. According to this embodiment, the second capacitor 312b is dimensioned for a voltage exceeding 100 V, and, more preferably, to withstand a voltage in the range of 75-1000 V.

Furthermore, a first antenna matching network 314a including matching circuits 316a is connected to the antenna 302 and to the first RF telemetry circuit 306a and is arranged to adjust the impedance of the antenna 302 to the impedance of the first RF telemetry circuitry 306a at the first frequency band at 400 MHz. By matching the antenna impedance to the impedance of the first RF telemetry circuitry 306a at the first frequency band, the reactance of the antenna 302 may be tuned out at that frequency so that the antenna 302 forms a resonant structure and efficiently transmits/receives far-field radiation. Preferably, the first capacitor 312a is incorporated into the first antenna matching network 314a and is connected in series with the matching circuits 316a. The first capacitor 312a is dimensioned to constitute a part of the antenna matching at the first frequency band.

In addition, a second antenna matching network 314b including matching circuits 316b is connected to the antenna 302 and to the second RF telemetry circuit 306b and is arranged to adjust the impedance of the antenna 302 to the impedance of the second RF telemetry circuitry 306b at the second frequency band at 2.45 GHz. By matching the antenna impedance to the impedance of the second RF telemetry circuitry 306b at the second frequency band, the reactance of the antenna 302 may be tuned out at that frequency so that the antenna 302 forms a resonant structure and efficiently transmits/receives far-field radiation. Preferably, the second capacitor 312b is incorporated into the first antenna matching network 314a and is connected in series with the matching circuits 316b. The second capacitor 312b is dimensioned to constitute a part of the antenna matching at the second frequency band.

According to one embodiment, the first capacitor 312a is dimensioned such that it attains its self resonating frequency at the 400 MHz frequency band and the second capacitor 312b is dimensioned such that it attains its self resonating frequency at 2.45 GHz. According to another embodiment, the second capacitor 312b is dimensioned such that it attains it self resonating frequency at 2.45 GHz, whilst the first capacitor 312a is dimensioned such that it has a capacitance in the region of 20-70 pF, or preferably in the region of 30-50 pF. The effect at 400 MHz will be that the impedance in the branch including the first RF telemetry circuitry 306a is low or even equal to the equivalent series resistance. The reactance at the branch including the second RF telemetry circuit 306b is typically −50 to −100 Ohm. The effect at 2.45 GHz will be that the impedance at the branch including the second RF telemetry circuit 306b is equal to the equivalent series resistance, whilst the impedance at the branch including the first RF telemetry circuitry 306a is a large inductance. Thus, the capacitors 312a and 312b will function as a component in a duplex filter separating the first and the second frequency.

Moreover, the RF telemetry circuits 306a, 306b and the controller 310 are connected to common ground 322, which, in turn, is connected to the housing 303. In this embodiment a third capacitor 318 is interposed between common ground 322 and the housing 203. The third capacitor 318 is arranged to withstand a voltage amplitude of a pulse conducted into the circuits via the housing 303 and common ground 322 and capable of modifying the state of or destroying components of the RF telemetry circuitry 306a, 306b, the controller 310, or the therapy circuit 305. Preferably, the third capacitor 318 is dimensioned to withstand a voltage exceeding 100 V, and, more preferably, to withstand a voltage in the range of 75-1000 V.

Preferably, the third capacitor 318 is dimensioned such that it attains its self resonating frequency at the frequency band employed by the first RF telemetry circuit 306a, for example, the 400 MHz band. The effect at 400 MHz will be that the impedance is low or equal to the equivalent series resistance.

According to a further embodiment of the present invention, the capacitor or the capacitors are arranged in the hermitically sealed feedthrough for the antenna.

Figure 4:
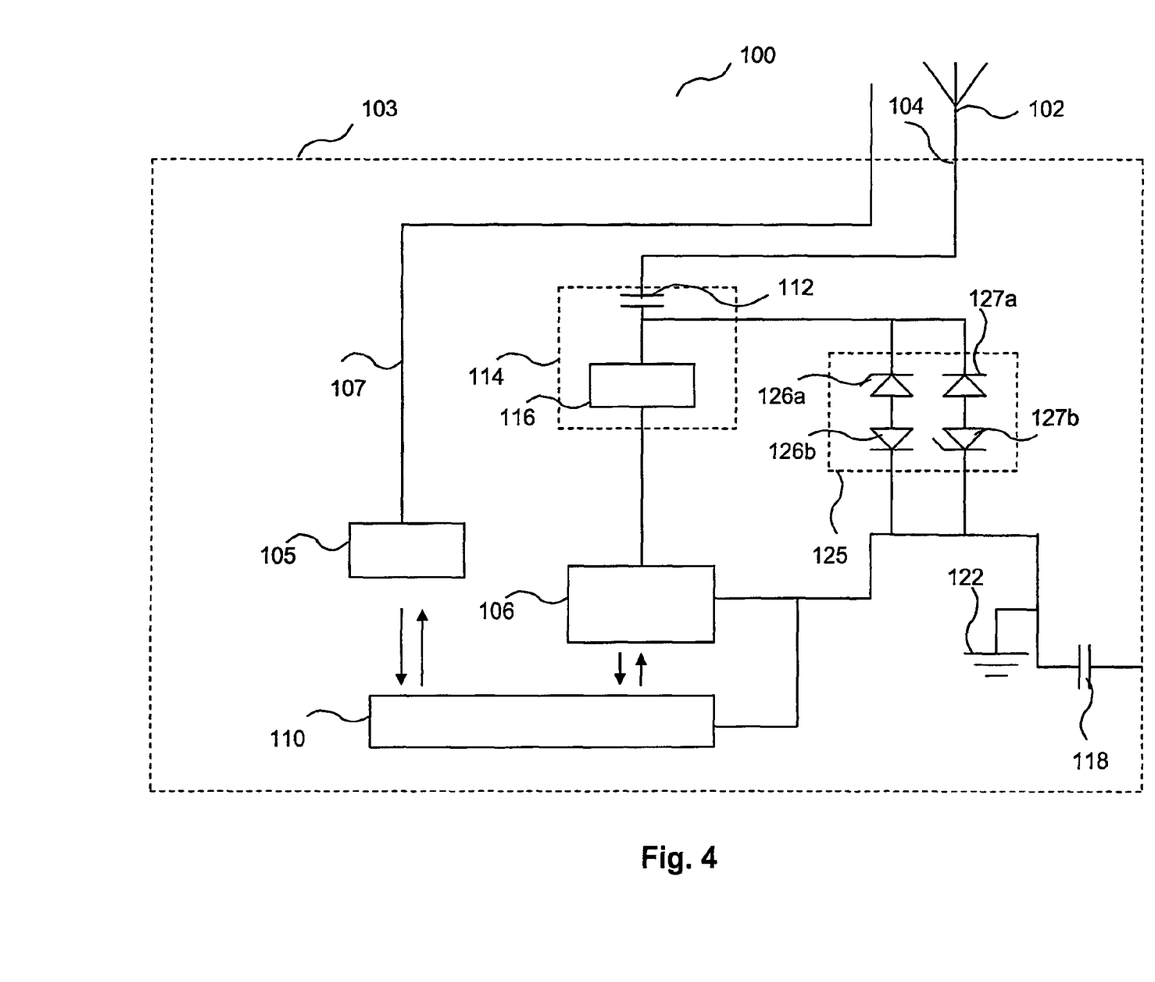
FIG. 4 diagrammatically shows fifth embodiment of the implantable medical device having protection circuits in accordance with the present invention.

Turning now to FIG. 4, a fifth embodiment of the present invention will be described. The same reference numerals for the parts, circuits and components included in the embodiments shown in FIGS. 1 and 4 are used and thus another description of these parts is not necessary.

According to this embodiment, a voltage suppressor circuit 125 is arranged between the first capacitor 112 and the second capacitor 118 as shown in FIG. 4. The circuit 125 comprises diodes 126a, 126b, 127a, 127b. Thereby, the protection of the circuitry of the medical device against voltage transients caused by e.g. defibrillation and/or electrocautery and conducted into the circuits via the housing 103 and common ground 122 is further improved.

The circuit 125 shown in FIG. 4, can also be arranged in any one of the embodiments shown in FIG. 1-3, or 5.

Figure 5A:
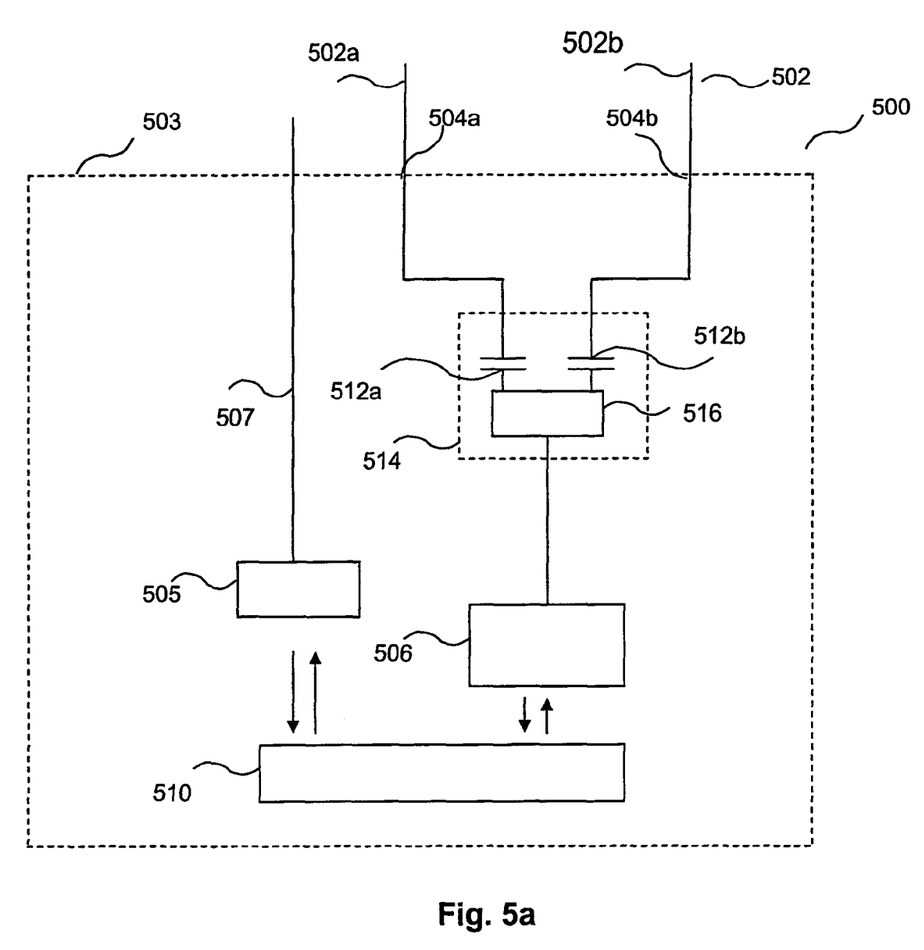
FIG. 5a diagrammatically shows an implantable medical device having a dipole antenna and comprising protection circuits for protecting the electronic circuitry of the device against undesired voltage pulses caused by exposure to defibrillation and/or electrocautery conducted into the device due to galvanic contact between the RF circuits of the device and tissue via the antenna in accordance with a further embodiment of the present invention.

Turning now to FIG. 5a, an implantable medical device having a dipole antenna and comprising protection circuits for protecting the electronic circuitry of the device against undesired voltage pulses caused by exposure to defibrillation and/or electrocautery conducted into the device due to galvanic contact between the RF circuits of the device and tissue via the antenna in accordance with a further embodiment of the present invention will be described.

The IMD 500 is provided with a dipole antenna 502a, 502b for communication with external devices such as an external programmer. Preferably, the antenna 502 is suitable for radiating and receiving far-field electromagnetic radiation. The antenna 502 is in direct tissue contact. The IMD 500 includes a hermetically sealed housing 503 provided with antenna feedthroughs 504a, 504b through which the antenna elements 502a, 502b are located and feedthroughs for medical leads, which housing 503 typically is formed of a biocompatible metal, e.g. titanium. The housing 503 contains a therapy circuitry 505 for providing particular functionality to the device such as cardiac rhythm management, or neuromuscular stimulation, RF telemetry circuitry 506 for providing RF communications. A battery (not shown) supplies power to the electronic circuitry within the housing 503. One or more leads 507 are connected to the therapy circuitry 505, which lead or leads 507 may be unipolar or bipolar, and may be adapted to operate in cooperation with a wide variety of implantable medical devices. Moreover, the lead or the leads 507 may include any of the passive or active fixation mechanisms known in the art for fixation of the lead 507 to the cardiac tissue when final position has been found. For example, the lead distal tip (not shown) may include a tined tip or a fixation helix. The leads 507 also carry one or more electrodes, such as a tip electrode or a ring electrode. The electrode senses electrical signals associated with depolarization and repolarization of the heart. In addition, the electrode may also transmit pacing pulses for causing depolarization of cardiac tissue adjacent to the electrode. Furthermore, the lead or leads 507 also comprises sensing means arranged to sense signals related heart activity.

A microprocessor controller 510 controls the operation of the therapy circuit 505, which includes sensing and stimulus generation circuitry that are connected to the electrodes of the lead or leads 507 for control of heart rhythm, and the RF telemetry circuitry for transmitting and receiving a carrier signal at a specific frequency modulated with telemetry data.

The controller 510 also outputs and receives the data contained in the modulated carrier generated or received by the RF telemetry circuitry 506. The RF telemetry circuitry 506 includes an RF transmitter and receiver that are connected to the antenna 503.

A capacitor 512a, 512b is connected in series with respective antenna element 502a, 502b and is arranged to withstand a voltage amplitude of a pulse received by the antenna 502a, 502b and capable of modifying the state of or destroying components of the RF telemetry circuitry 506, the controller 510, or the therapy circuit 505. Preferably, the capacitors 512a, 512b are dimensioned to withstand a voltage exceeding 100 V, and, more preferably, to withstand a voltage in the range of 75-1000 V.

Furthermore, an antenna matching network 514 including matching circuits 516 arranged to adjust the impedance of the antenna 502a, 502b to the impedance of the RF telemetry circuitry 506 is connected to the antenna 502a, 502b and to the RF telemetry circuit 506. The antenna matching network 514 loads the antenna 502a, 502b with an amount of inductance or capacitance to thereby adjust the effective electrical length of the antenna, and hence the resonance frequency of the antenna. By matching the antenna impedance to the impedance of the RF telemetry circuitry at a specific carrier frequency, the reactance of the antenna may be tuned out at that frequency so that the antenna forms a resonant structure and efficiently transmits/receives far-field radiation.

Figure 5B:
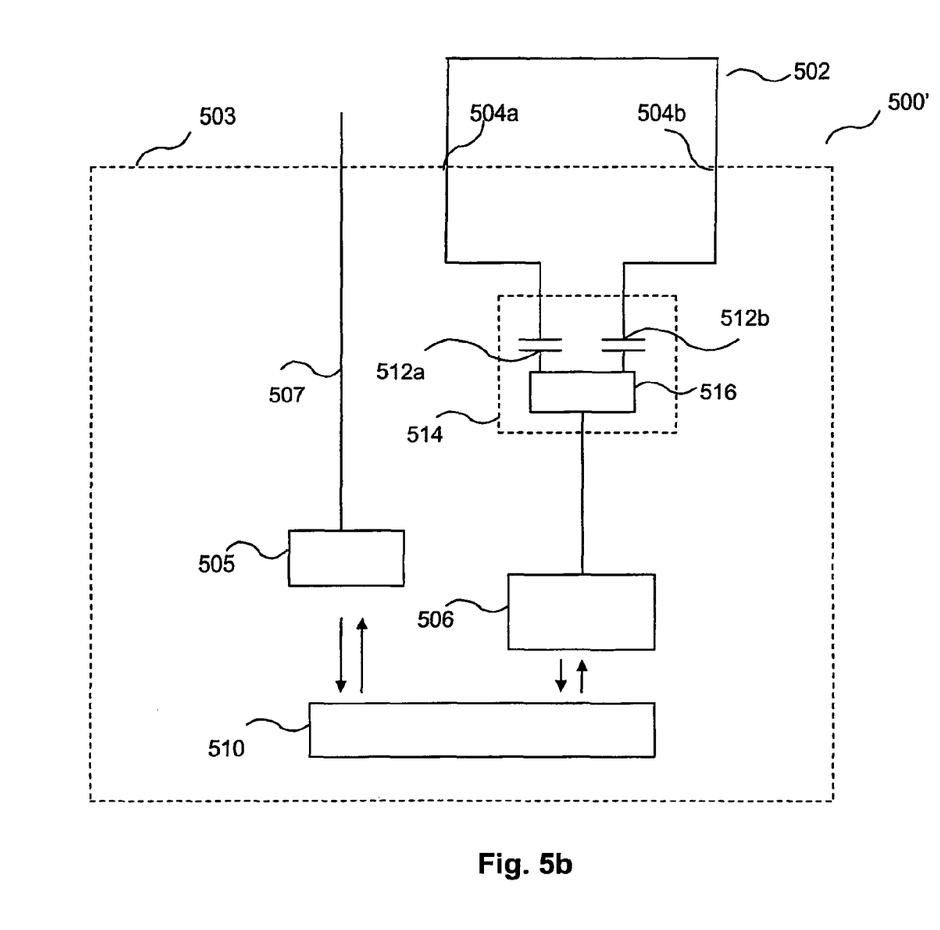
FIG. 5b diagrammatically shows an implantable medical device having a loop antenna and comprising protection circuits for protecting the electronic circuitry of the device against undesired voltage pulses caused by exposure to defibrillation and/or electrocautery conducted into the device due to galvanic contact between the RF circuits of the device and tissue via the antenna in accordance with yet another embodiment of the present invention.

As shown in FIG. 5b, the implantable medical device 500' is provided with a loop antenna 502. Remaining parts and elements shown in FIG. 5b are similar or the same as in the embodiment shown in FIG. 5a so another description thereof is not necessary.

Although modifications and changes may be suggested by those skilled in the art, it is the invention of the inventor to embody within the patent warranted heron all changes and modifications as reasonably and properly come within the scope of his contribution to the art.

I claim as my invention:

1. An implantable medical device comprising:
    at least one electronic circuit having a connection to a common ground;
    at least one RF telemetry circuit having a connection to said common ground;
    at least one RF telemetry antenna configured to be in contact with tissue when said medical device is implanted, said at least one RF telemetry antenna comprising a plurality of device parts capable of functioning as an antenna, each of said parts being configured to be in contact with tissue when said medical device is implanted, and each of said parts being capable of receiving a pulse having a voltage amplitude that is capable of modifying a state of, or destroying, any component in said electronic circuit or said RF telemetry circuit; and
    each of said parts of said at least one RF telemetry antenna that is capable of functioning as an antenna being connected to said RF telemetry circuit via at least one capacitor, said capacitor being dimensioned to withstand the voltage amplitude of said pulse in order to prevent said pulse from being transmitted to said RF telemetry circuit via any of said parts of said RF telemetry antenna, and further comprising at least one further capacitor connected in series with said at least one RF telemetry antenna and dimensioned to withstand a voltage of at least one hundred volts.

2. An implantable medical device as claimed in claim 1 comprising a housing, and wherein said at least one capacitor is connected to said housing and to said common ground.

3. An implantable medical device as claimed in claim 1 comprising at least one antenna matching network containing said at least one further capacitor.

4. An implantable medical device as claimed in claim 1 comprising a feedthrough for said antenna, and wherein said at least one further capacitor is disposed in said feedthrough.

5. An implantable medical device comprising:
    at least one electronic circuit having a connection to a common ground;
    at least one RF telemetry circuit having a connection to said common ground;
    at least one RF telemetry antenna configured to be in contact with tissue when said medical device is implanted, said at least one RF telemetry antenna comprising a plurality of device parts capable of functioning as an antenna, each of said parts being configured to be in contact with tissue when said medical device is implanted, and each of said parts being capable of receiving a pulse having a voltage amplitude that is capable of modifying a state of, or destroying, any component in said electronic circuit or said RF telemetry circuit;
    each of said parts of said at least one RF telemetry antenna that is capable of functioning as an antenna being connected to said RF telemetry circuit via at least one capacitor, said capacitor being dimensioned to withstand the voltage amplitude of said pulse in order to prevent said pulse from being transmitted to said RF telemetry circuit via any of said parts of said RF telemetry antenna, and further comprising at least one further capacitor connected in series with said at least one RF telemetry antenna;
    wherein said at least one radio frequency telemetry antenna is configured for communication in at least two predetermined frequency bands, and comprising a first antenna matching network tuned to a first of said frequency bands, and a second antenna matching circuit tuned to a second of said frequency bands; and
    wherein said at least one further capacitor is connected to be self-resonant in said first of said frequency bands.

6. An implantable medical device comprising:
    at least one electronic circuit having a connection to a common ground;
    at least one RF telemetry circuit having a connection to said common ground;
    at least one RF telemetry antenna configured to be in contact with tissue when said medical device is implanted, said at least one RE telemetry antenna comprising a plurality of device parts capable of functioning as an antenna, each of said parts being configured to be in contact with tissue when said medical device is implanted, and each of said parts being capable of receiving a pulse having a voltage amplitude that is capable of modifying a state of, or destroying, any component in said electronic circuit or said RF telemetry circuit;
    each of said parts of said at least one RF telemetry antenna that is capable of functioning as an antenna being connected to said RF telemetry circuit via at least one capacitor, said capacitor being dimensioned to withstand the voltage amplitude of said pulse in order to prevent said pulse from being transmitted to said RF telemetry circuit via any of said parts of said RF telemetry antenna;
    wherein said at least one capacitor is dimensioned to withstand a voltage of at least one hundred volts.

7. An implantable medical device comprising:
    at least one electronic circuit having a connection to a common ground;
    at least one RF telemetry circuit having a connection to said common ground;
    at least one RF telemetry antenna configured to be in contact with tissue when said medical device is implanted, said at least one RF telemetry antenna comprising a plurality of device parts capable of functioning as an antenna, each of said parts being configured to be in contact with tissue when said medical device is implanted, and each of said parts being capable of receiving a pulse having a voltage amplitude that is capable of modifying a state of, or destroying, any component in said electronic circuit or said RF telemetry circuit;
    each of said parts of said at least one RF telemetry antenna that is capable of functioning as an antenna being connected to said RF telemetry circuit via at least one capacitor, said capacitor being dimensioned to withstand the voltage amplitude of said pulse in order to prevent said pulse from being transmitted to said RF telemetry circuit via any of said parts of said RF telemetry antenna;

wherein said at least one RF telemetry antenna is configured for communication in at least two predetermined frequency bands, and wherein said implantable medical device comprises:
- a first antenna matching network tuned for a first of said frequency bands and comprising a further, first capacitor connected in series with said at least one RF telemetry antenna; and
- a second antenna matching network tuned for a second of said frequency bands and comprising a further, second capacitor connected in series with said at least one RF telemetry antenna.

8. An implantable medical device as claimed in claim 7 wherein said further, first capacitor is connected to be self-resonant at said first of said frequency bands and said further, second capacitor is connected to be self-resonant at said second of said frequency bands.

9. An implantable medical device as claimed in claim 7 wherein said further, first capacitor has a capacitance in a range between 20 and 70 pF, and said further, second capacitor is connected to be self-resonant at said second of said frequency bands.

10. An implantable medical device comprising:
- at least one electronic circuit having a connection to a common ground;
- at least one RF telemetry circuit having a connection to said common ground;
- at least one RF telemetry antenna configured to be in contact with tissue when said medical device is implanted, said at least one RF telemetry antenna comprising a plurality of device parts capable of functioning as an antenna, each of said parts being configured to be in contact with tissue when said medical device is implanted, and each of said parts being capable of receiving a pulse having a voltage amplitude that is capable of modifying a state of, or destroying, any component in said electronic circuit or said RF telemetry circuit;
- each of said parts of said at least one RF telemetry antenna that is capable of functioning as an antenna being connected to said RF telemetry circuit via at least one capacitor, said capacitor being dimensioned to withstand the voltage amplitude of said pulse in order to prevent said pulse from being transmitted to said RF telemetry circuit via any of said parts of said RF telemetry antenna;
- wherein said at least one RF telemetry antenna is configured for communication in at least two predetermined frequency bands, and wherein said device comprises a housing and wherein said at least one capacitor is connected to said housing and to said common ground and is connected to be self-resonant at a first of said frequency bands.

* * * * *